United States Patent [19]

Grandics et al.

[11] Patent Number: 5,466,377

[45] Date of Patent: Nov. 14, 1995

[54] CHROMATOGRAPHY MEDIA AND THEIR USES

[76] Inventors: Peter Grandics; Susan Szathmary, both of P.O. Box 1924, Arcadia, Calif. 91077

[21] Appl. No.: 183,365

[22] Filed: Jan. 19, 1994

[51] Int. Cl.[6] .................................................. B01D 15/08
[52] U.S. Cl. ........................ 210/635; 210/656; 210/198.2
[58] Field of Search .................................... 210/635, 656, 210/198.2, 502.1, 659; 530/413, 417

[56] References Cited

U.S. PATENT DOCUMENTS

| | | | |
|---|---|---|---|
| 3,597,350 | 8/1971 | Determann | 210/635 |
| 3,598,245 | 8/1971 | Determann | 210/635 |
| 5,328,603 | 7/1994 | Velander | 210/198.2 |

Primary Examiner—Ernest G. Therkorn

[57] ABSTRACT

A method as well as large bead chromatography particles are described for the direct capture of a desired product from unclarified process liquor on standard, low pressure, packed bed chromatography columns. The beads are sufficiently large so that the particulate contaminants can flow in the interparticle lumen and exit the column without obstructing the flow. The desired product is simultaneously captured by the functional groups of the beads. The beads have high dynamic capacities and allow rapid processing of large volumes of process materials.

21 Claims, 10 Drawing Sheets

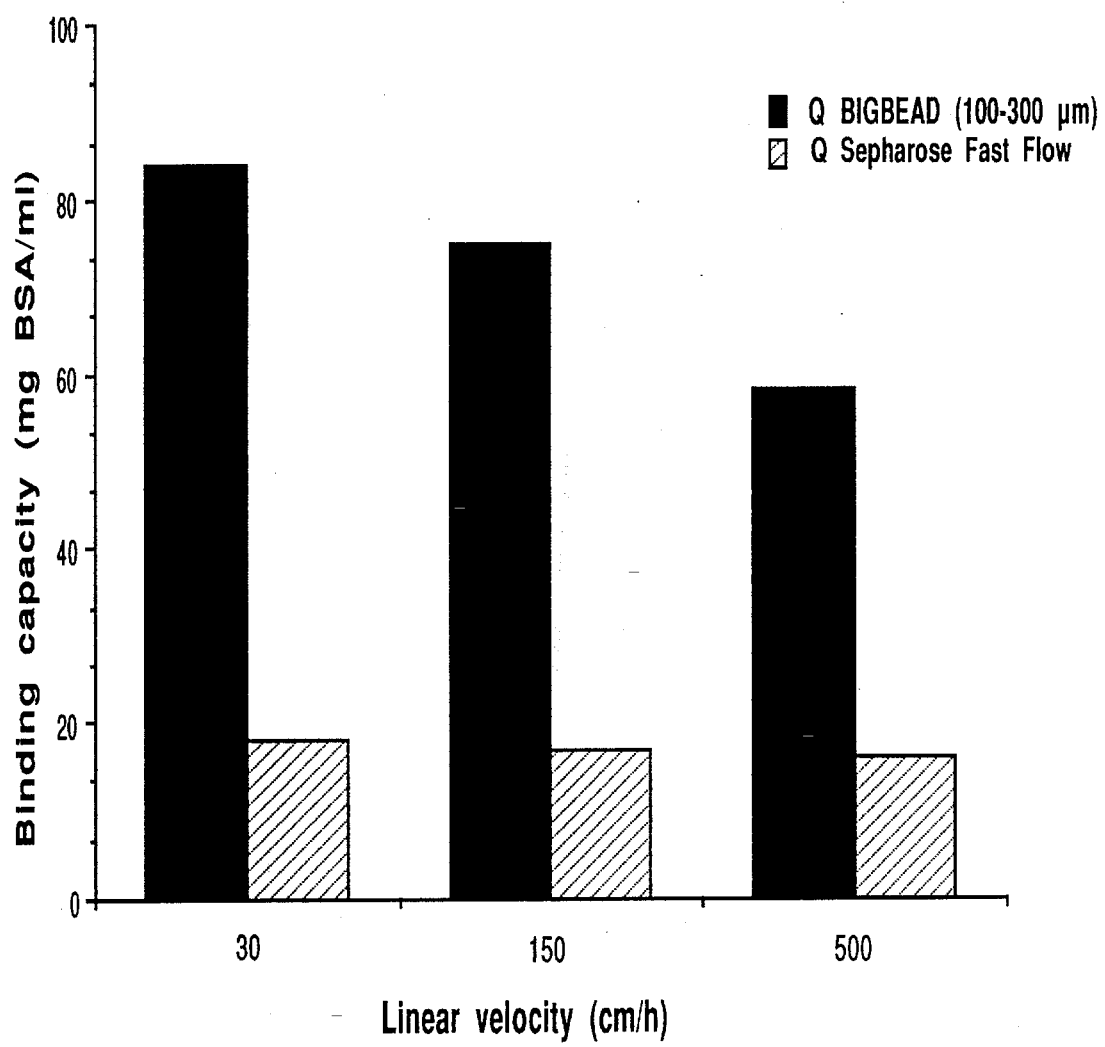

Monoclonal Antibody Purification on SP BIGBEAD (300-500 μm)

Conditions:

Cell density: $3 \times 10^6$ hybridoma per ml
Bed volume: 9 ml
Column diameter: 1.5 cm
Buffer A: 20 mM citrate, pH 5.0
Buffer B: 20 mM Tris, 0.3 M NaCl, pH 7.5
Sample volume: 200 ml
Loading speed: 400 cm/h
Elution speed: 30 cm/h
Wash speed: 3,000 cm/h
Wash volume: 120 ml

Albumin Purification from Yeast Cell Suspension Using Q BIGBEAD (300-500 μm)

Conditions:

Cell density: $10^8$ yeast cells per ml
Bed volume: 9 ml
Column diameter: 1.5 cm
Buffer A: 20 mM Tris, pH 8.0
Buffer B: 20 mM Tris, 0.3 M NaCl, pH 8.0
Sample volume: 600 ml
Loading speed: 500 cm/h
Elution speed: 50 cm/h
Wash speed: 3,000 cm/h
Wash volume: 120 ml

Recombinant Fab Purification on SP BIGBEAD (800-1100 μm)

Conditions:

Cell density: 100 OD *E. coli* per ml
Bed volume: 9 ml
Column diameter: 1.5 cm
Buffer A: 20 mM citrate, pH 5.0
Buffer B: 20 mM Tris, 0.3 M NaCl, pH 7.5
Sample volume: 300 ml
Loading speed: 400 cm/h
Elution speed: 30 cm/h
Wash speed: 3,000 cm/h
Wash volume: 140 ml

Purification of Serum Albumin on DEAE BIGBEAD (100-300 μm)

Conditions:

Bed volume: 5 ml
Column diameter: 1.5 cm
Buffer A: 20 mM phosphate, pH 7.0
Buffer B: A+ 0.3 M NaCl, pH 7.0
Sample volume: 20 ml
Loading speed: 30 cm/h
Elution speed: 30 cm/h
Yield: 574 mg albumin

CHROMATOGRAPHY MEDIA AND THEIR USES

BACKGROUND OF THE INVENTION

This invention is directed to chromatographic media and method for direct processing of crude feeds on columns for isolation of biologically active materials.

Traditionally, downstream processing of biologics from cell culture/fermentation harvests has required two major operations: recovery and purification. Recovery involves the removal of cellular and other particulate materials by centrifugation and/or microfiltration, as well as an initial volume reduction step, typically ultrafiltration. Since conventional chromatography media are rapidly fouled by cell debris, particle-free feed must be prepared for the purification operation.

Centrifugation and filtration are not only lengthy and costly operations, they compromise quality. Proteases released from broken cells can degrade the target protein, further complicating the task of purification method development and increasing purification costs. The longer the contact time with the concentrated cellular debris, the more product may be lost.

Direct capture of the protein product from the unclarified feed would minimize product degradation and improve product quality, yield and process economy. Also, the capital-intensive recovery operation would be greatly simplified if the product capture and cell removal steps were combined into a single operation.

There are two approaches to directly capture product from unclarified feed, such as cell culture/fermentation harvest or other biological sample (e.g., blood plasma). One proposes fluidization of the capture resin particles. Via fluidization, the individual particles are separated so that the debris can exit the column bed unobstructed.

This approach suffers from several problems. The product breaks through the fluidized bed early on due to channelling, causing product loss. The fluidized bed system operates at a predetermined low flow rate, i.e., there is no flexibility in the operation or means for changing the size of the column. The buffer consumption of the system is higher than on packed bed systems, which is a significant cost factor for high value pharmaceutical products, many of which require specialized buffers for their purification. Fluidized bed operation also requires specialized, costly hardware and chromatography media.

The other approach is the use of packed bed columns for particulate removal. This avenue has remained unexplored for the following reason. To clear cellular debris on a packed bed column requires using large, preferably spherical particles. These particles require sufficient space in the interparticle lumen to let cells or other particulates of comparable size to exit the column.

The downside of using large particles (beads) is that the protein binding capacity is a function of the available surface per unit volume of gel bed. Therefore with increased particle diameters a loss of binding capacity is observed. When the particle diameter is increased from 0.1 mm to 1 mm, such as is required to handle dense cell suspensions, approximately 90% of the protein binding capacity is lost. This made packed bed columns impractical for processing crude process feed streams.

Packed bed column operation, however, offers simplicity, efficiency and economy. It is flexible and easy to scale. There is no need for specialized particles, equipment or training of the operators. The production floor-space is relatively small for standard chromatography and there is no need for the modification of the height of the production facility to accommodate the fluidized bed equipment.

Product application rate is another important issue in terms of throughput of the operation. This is predetermined for fluidized bed systems, but for packed column systems just the reaction binding kinetics is the rate limiting factor. This allows higher throughput, up to 3–10 times higher than for fluidized bed systems.

Crude biological feed streams often have a physiological ionic strength which is too high in many situations to allow direct binding of the protein of interest to ion exchange media. Therefore, dilution of the feed with deionized water is required, typically 3–5 times. This greatly increases the total volume of the feed to be processed and partially offsets the advantage of direct processing versus the traditional centrifugation-filtration-concentration route. Ionic strength reduction in the crude feed stream other than dilution is therefore desirable.

An alternative method for reducing ionic strength is dialysis. However, dialysis is impractical with unclarified feed streams as particulate matter will rapidly clog dialysis membranes. Therefore, with current technologies the only practical method for ionic strength reduction in crude feed streams is dilution.

There is therefore a need for improved chromatographic materials and methods to achieve direct processing of crude feeds, such as cell culture/fermentation harvests tissue extracts, or blood plasma, on packed bed columns. There is also a need for ion removal from crude samples without dilution and the resulting loss of throughput.

SUMMARY OF THE INVENTION

Chromatography media and methods have been developed for direct processing of unclarified crude feed streams, including cell/fermentation harvest, tissue extracts, and plasma/blood. The novel, large bead chromatography media are packed into a standard, low pressure chromatography column in which end-plate screens are replaced with large pore screens (60–180 µm pores). The large pores prevent column blockage. Because particle sizes are large, the cellular material flows between the beads in the interparticle lumen, while the soluble product is captured by the functional groups on the beads.

After product capture, residual cellular material is removed by brief high-speed wash pulses. The product is then eluted by typical elution methods. Thus, the novel, large-bead chromatography resins allow direct processing of cell culture or fermentation broth as well as other unclarified feeds in a packed bed column by combining cell removal with simultaneous product capture.

By changing the particle size ranges utilized, solids of different concentrations can be removed. The novel beads overcome the drastic loss of protein binding capacity which is observed with traditional ion exchange media as the particle diameter is increased from 50 µm to 500 or 1000 µm. Also, the beads exhibit a greatly improved static to dynamic binding capacity ratio. The loss of binding capacity in the dynamic mode of operation is greatly reduced relative to conventional polysaccharide ion exchange media (agarose adsorbents such as Sepharose™).

In general, a process according to the invention comprises:

(1) packing a large bead capture chromatography medium into low pressure chromatography columns;

(2) conditioning an unclarified process liquor having a high physiological ionic strength and containing a desired soluble product, as well as possibly containing particulate materials, so that the product can be adsorbed onto the capture chromatography medium;

(3) adding processing aid so that the inhibition of soluble product binding to the capture medium by cellular components is overcome;

(4) applying the conditioned process liquor onto the chromatography column under conditions such that the soluble product adsorbs to the capture chromatography medium;

(5) allowing particulate materials in the unclarified process liquor to exit the column in the interparticle space;

(6) removing residual entrapped particles from the column via high speed reverse wash pulses; and (7) eluting product from the capture chromatography medium by changing binding conditions so that the product is removed from the column.

BRIEF DESCRIPTION OF THE DRAWINGS

The accompanying drawings illustrate the invention and its results regarding the practical application of the invention.

FIG. 1B exhibits the bovine serum albumin binding capacities of strong anion exchange BIGBEAD™ (100–300 μm) media. For the albumin binding test, 9 ml bed volume columns (1.5 cm diameter) were used at selected linear velocities. Buffer A was 20 mM Tris, pH 8.0; Buffer B was 20 mM Tris, pH 8.0, 0.3M NaCl. Albumin, 1 g, dissolved in Buffer A at 10 mg/ml was applied to each column. After washing, bound protein was eluted and quantitated. The amount of protein eluted was plotted against flow rates.

DESCRIPTION

Figure 1A:
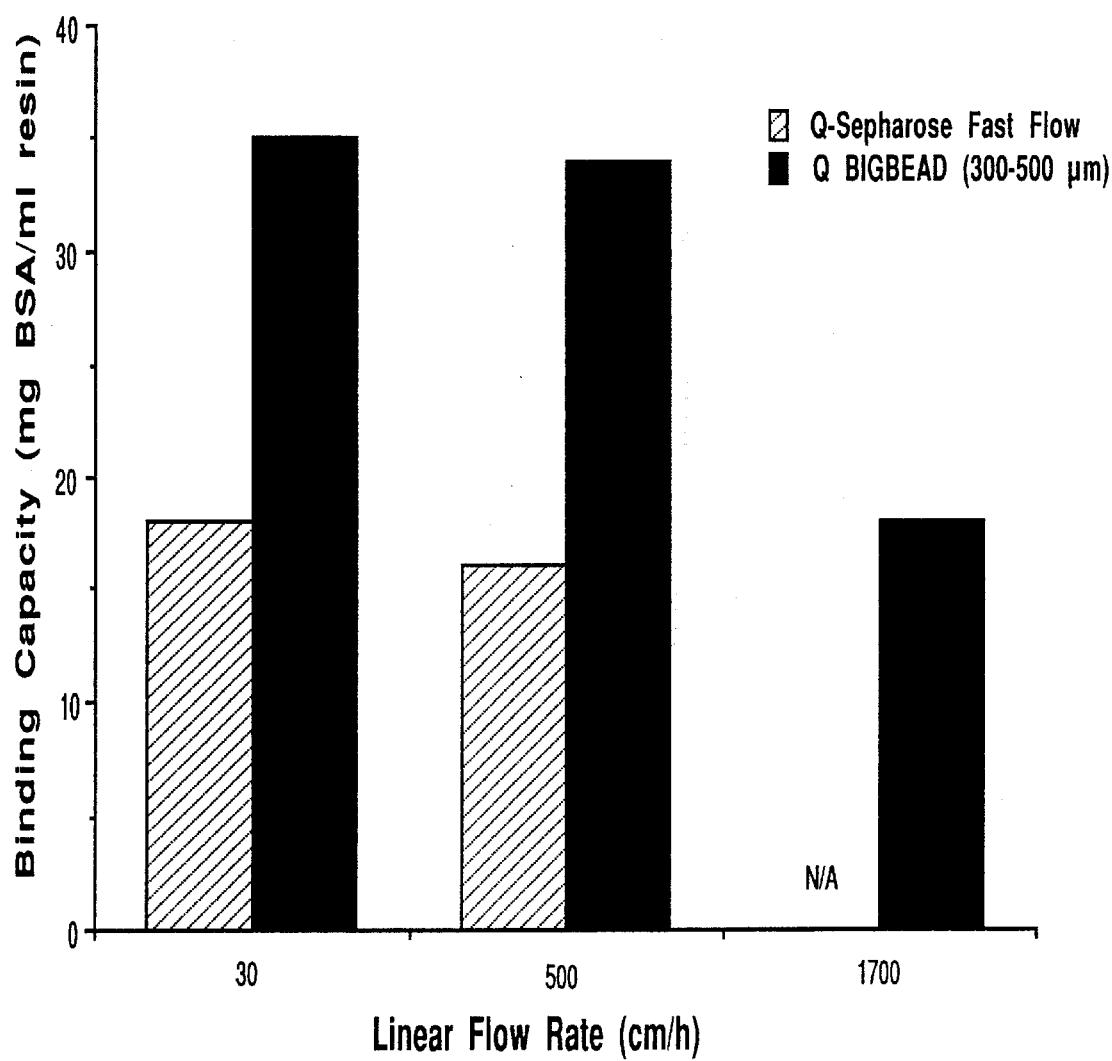
FIG. 1A demonstrates the bovine serum albumin binding capacities of strong anion exchange BIGBEAD™ (300–500 μm) media. For the albumin binding test, 9 ml bed volume columns (1.5 cm diameter) were used at selected linear velocities. Buffer A was 20 mM Tris, pH 8.0; Buffer B was 20 mM Tris, pH 8.0, 0.3M NaCl. Albumin, 500 mg, dissolved in Buffer A at 10 mg/ml was applied to each column. After washing, bound protein was eluted and quantitated. The protein amounts eluted were plotted against the flow rates.

In accordance with the subject invention, components and methods are provided for direct processing of crude biological feed streams on standard, packed bed column chromatography. The invention describes large bead, hardened agarose chromatography media, with ion exchange groups attached through a spacer arm. Hardening gives the matrix increased chemical and mechanical stability. The beads are made to sizes exceeding those of standard agarose chromatography beads. The practically useful bead size ranges are about 100 to about 1100 μm; more precisely 100–300 μm, 300–500 μm, 500–800 μm and 800–1100 μm size ranges are preferred. The objective of using the large bead sizes is to create sufficiently large space between the individual beads to let particulate contaminants freely flow through the column.

The method of the present invention provides for the capture and elution of a desired product from an initial unclarified process liquor. The desired product can be a protein, such as an antibody, a receptor protein, an enzyme, or a recombinant bacterial protein. However, methods according to the present invention can also be for the isolation of other products of biological interest.

The chromatography medium to which the desired product binds, by ion-exchange or other interactions, is referred to herein as the capture chromatography medium to distinguish it from other chromatography media used herein.

Therefore, the size of the particle of the capture chromatography medium primarily determines the concentration of the solids which can flow through the column without causing obstruction in the flow. If the cell density in the process liquor is below $10^9$ cells per ml, the 300–500 μm particle size range is suitable for removing particulate contaminants. This situation is common in mammalian cell culture or low density yeast fermentations.

The particulate contaminants to be removed can be cells, cell fragments, aggregated proteins, denatured proteins, precipitated proteins, lipids, or nucleic acids. Cells to be removed can be of bacterial, yeast, or mammalian origin. A particularly significant type of cell of mammalian origin to be processed is blood cells.

Bacterial fermentations can produce cell densities two orders of magnitude higher (100 OD units per ml cell density). In many biotechnology applications high density bacterial fermentation is used producing cell densities up to 20% solids. The higher solids content necessitates using larger beads for the capture chromatography medium, in the range of 800–1100 μm.

On the other hand, the process liquor may also contain particulate contaminants which are smaller than cells or cell constituents. These may be protein aggregates or precipitated proteins, or lipid micelles. Examples of samples containing such particulate contaminants are blood plasma or tissue extracts. To handle these conditions, a smaller particle size range is suitable. Most preferred is a 100–300 μm particle size range.

Typically, the large bead capture media have high dynamic product binding capacities in the linear velocity range of 1–1000 cm/h. Preferably, the loss of binding capacity of said capture media is less than 30% from static to 500 cm/h linear velocity.

When an unclarified process feed stream is applied to a suitably selected large bead ion exchange column, particles in the feed stream can flow down in the interparticle lumen and exit the column. However, a small fraction of the particulate matter remains entrapped in the column bed and needs to be removed before elution can commence. The removal of the entrapped solids can be effected with high speed wash pulses with occasional changing of the direction of the flow on the column.

When challenged with a crude feed mixture containing $10^9$ yeast cells per ml feed, 99.9999% of the cells are removed from a Q BIGBEAD column after washing.

Elution is typically performed by changing the binding conditions so that the product is removed from the capture chromatography medium. Typically, this is performed by changing the pH and/or the ionic strength of the solution in contact with the column so that the interactions that caused the product to bind to the column are neutralized. For example, in the case of an anion exchanger, if the pH is lowered, negatively charged groups on the product become protonated and the product dissociates from the column because the product is no longer an anion. Other elution conditions are well known in the art for particular types of ion exchange columns as well as other columns and need not be described further here.

Therefore, subsequent purification steps may employ conventional small bead (50–150 μm) adsorbents without further treatment of the eluate. The very low concentrations of particles in the eluted protein will clear during the next purification step, regardless of the adsorbents used.

For optimal clearance of particulates, the proper column dimensions need to be selected. Since the column bed acts as a depth filter, it is counterproductive to pack a column that is too tall. A chromatography column with a bed height versus bed diameter ratio of 4 or less is optimal. The original screens on the column endpieces are preferably replaced with 60–180 μm porosity screens to avoid fouling.

Column packing can be carried out by conventional procedures, either by gravity or pressure packing. The column should be equilibrated with the starting buffer by passing 5 bed volumes of starting buffer through the column at 500–1,000 cm/h in the best mode of operation. The flow rate versus back pressure curve is given in FIG. 2.

Before loading, the feed stream must be conditioned in order to allow the desired protein to bind to the column. This can be achieved by simply diluting the feed stream with deionized water and adjusting the pH of the feed stream before application to the capture column. Since the largest volumes need to be processed at the front end of the purification, i.e., in the initial steps, dilution of the feed can greatly increase the total volume to be processed (3–5 times). This can increase loading times to such an extent that much of the advantage of direct processing would be lost. Therefore, it is desirable to achieve sample conditioning without increasing the already large initial feed volumes.

We observed that with increasing bead sizes the protein binding capacity of ion exchange media diminishes. Therefore, if the bead size of the ion exchanger is sufficiently large and the porosity is sufficiently small, the binding capacity for proteins will be negligible while the small ion binding capacity remains high. The large particle sizes are also necessary for clearing particulate contaminants. Cation and anion exchange particles, in the $H^+$ and $OH^-$ forms respectively, of appropriate bead sizes, can be mixed in the molar ratio of 1:1 providing a mixed bed ion exchanger which can reduce the ionic strength (conductivity) of the starting fermentation/cell culture harvest (with small pH changes) to the level required for efficient binding of the target protein to the capture resin. Typically, the starting fermentation or cell culture harvest medium has a high ionic strength that is in the physiological range.

Preferably, the large bead mixed bed ion exchange resin has capacity for the product sufficiently low so that less than about 5% of the protein loaded is bound.

The ion removing beads can be made out of polymers, such as polystyrene or acrylic compounds or natural sources, such as polysaccharides, or silica. The particles can be used in the mode of packed column or batchwise, i.e., stirred into the feed stream and then separated off on a large pore funnel.

Figure 7:
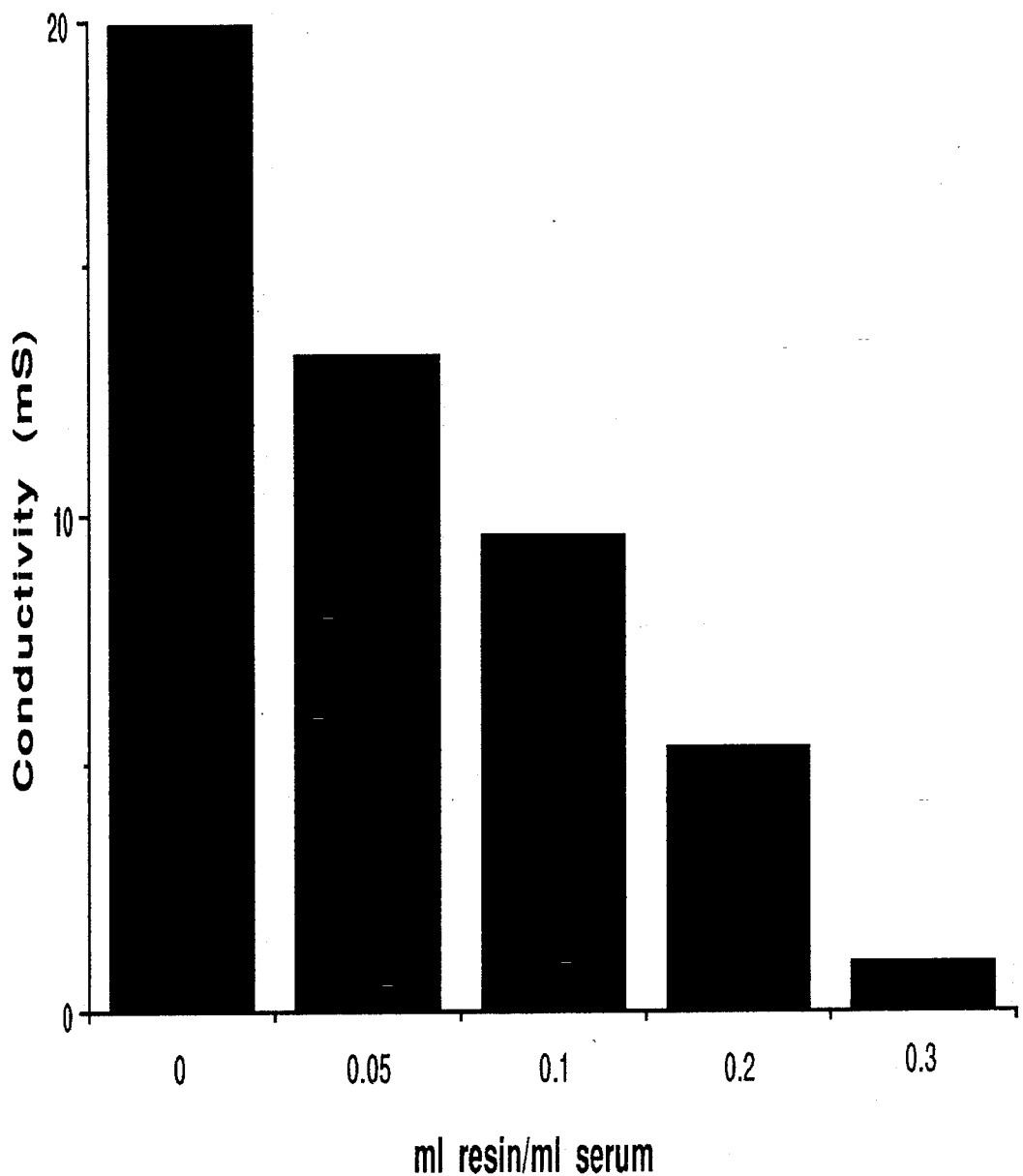
FIG. 7 is a graph exhibiting how the conductivity of swine serum was reduced with the addition of increasing volumes of ion removing BIGBEAD™ resin. To 100 ml whole serum, ion removing BIGBEAD™ resin was added in equal increments and gently stirred for 20 min. Conductivity and pH were measured after every incubation. The conductivity of serum was approximately 20 mS. The pH remained neutral up until 0.2 ml resin was added per ml serum. When larger amounts of resin were added (0.3 ml per ml serum), the pH began turning slightly acidic, to 5.3. Therefore, pH monitoring and adjustment is necessary at higher resin to serum (feed) ratios.
Figure 8:
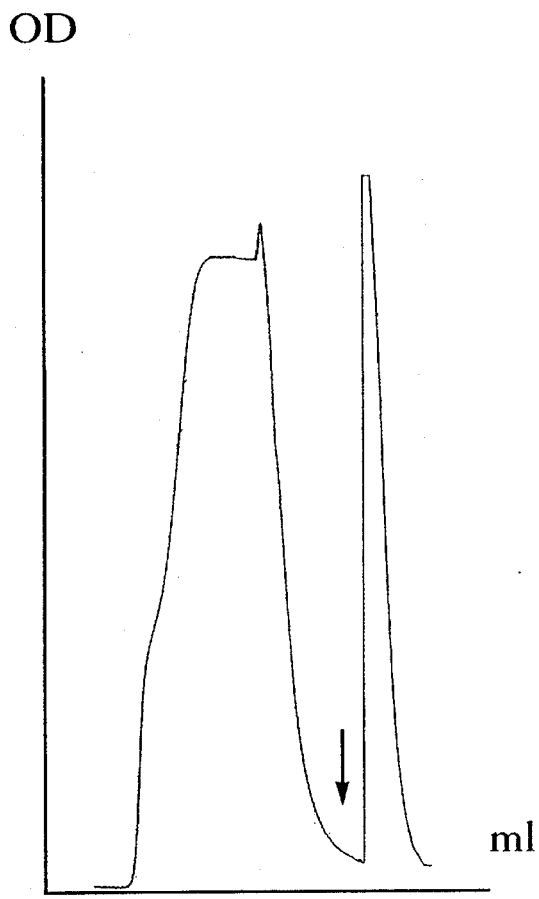
FIG. 8 is a chromatogram of the separation of albumin from swine serum. Serum was treated with ion removing BIGBEAD™ as shown in FIG. 7 and conductivity was reduced to 3 mS. Treated serum was chromatographed on DEAE BIGBEAD™ (100–300 μm) resin equilibrated with 20 mM phosphate, pH 7.0 (equilibration) buffer. After washing with the equilibration buffer, bound albumin was eluted with a 20 mM phosphate, 0.3M NaCl, pH 7.0 buffer. In the column flowthrough, an IgG rich fraction, in the eluate an albumin rich fraction was obtained. The purity of albumin was 85–90% by SDS-PAGE (not shown) with a yield of approximately 95%.
Figure 9:
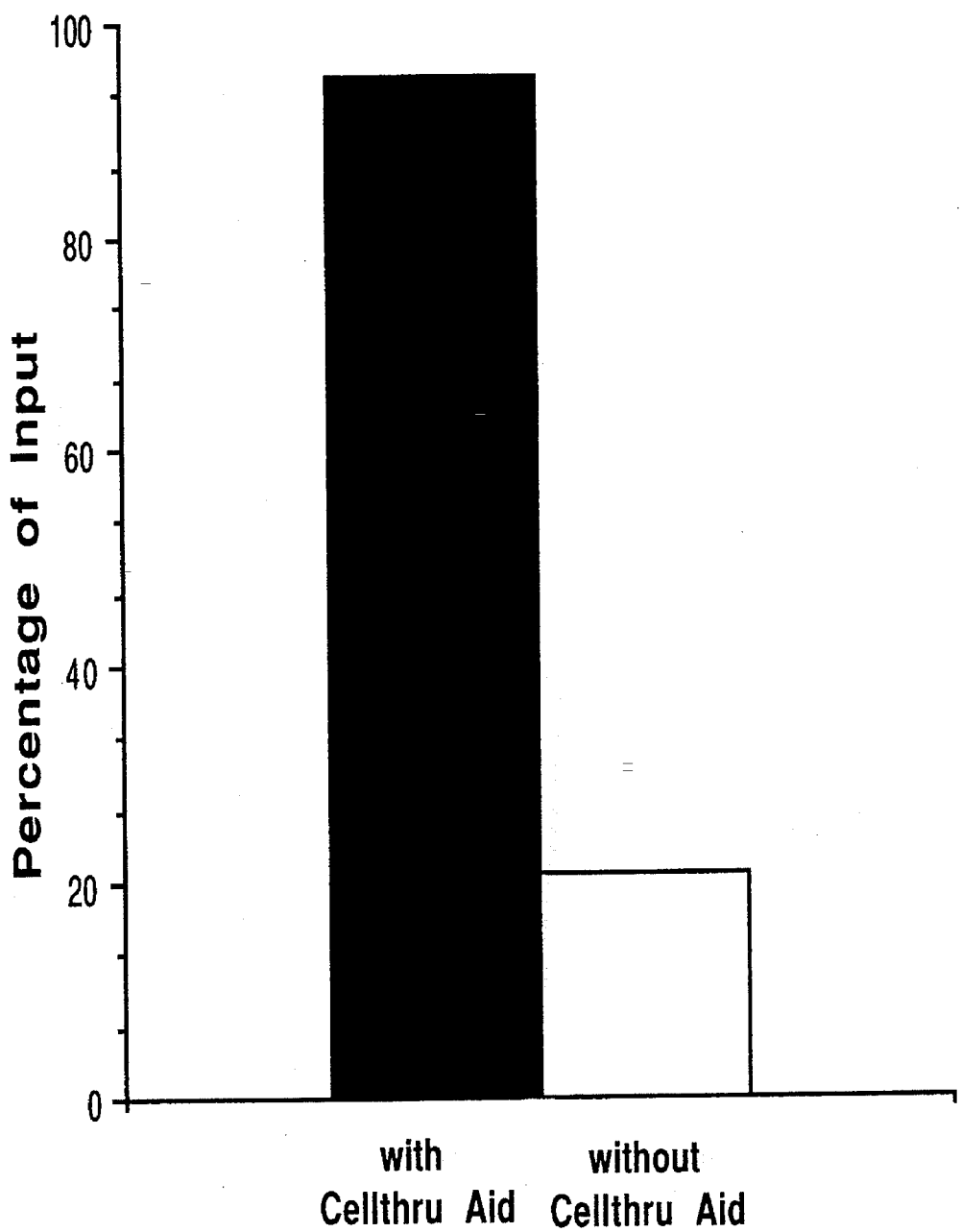
FIG. 9 is a graph showing the increased efficiency of the capture large bead ion exchange media with the addition of 0.1% (v/v) of the processing aid. The aid allows the full utilization of the binding capacity of the resin which is diminished by the presence of cellular materials.

Batch use is most effective with highly viscous feeds, like blood plasma. FIG. 7 demonstrates the effective use of these beads in reducing the conductivity of plasma to the level which allows subsequent binding of albumin to a DEAE anion exchange column (FIG. 8). Besides reducing conductivity, the loading pH may also need to be adjusted for efficient sample binding.

Application of the conditioned crude feed to the capture large bead ion exchange column is possible at various linear velocities. The preferred linear velocity range is 30–2,000 cm/h, most preferably 300–1,000 cm/h. Higher loading speeds are, of course, possible, but the binding capacity may be reduced. The capture column can be operated at a low pressure, even at high flow rates.

The large bead capture ion exchange media can be made out of polymers, such as polystyrene or acrylic compounds or natural compounds, such as polysaccharides or silica. In the Examples, polysaccharide (agarose) based large particles were used (manufactured by Sterogene Bioseparations, Inc., Arcadia, Calif.) The agarose particles from Sterogene, besides their larger size, have surface characteristics different from all the other sources of agarose particles.

When these particles are derivatized with standard ion exchange chemistries (e.g., DEAE or CM), the resulting ion exchange beads behave as if the diffusion limitation of conventional agarose beads was relieved. This phenomenon needs further investigation but it is clearly not pore dependent as the size exclusion characteristics of the Sterogene agarose beads are indistinguishable from other standard agarose particles (e.g., Sepharose™ (Pharmacia)).

These result in agarose ion exchange media with very high dynamic capacities for protein. If the 300–500 µm bead Q and SP BIGBEAD™ media dynamic protein binding capacities two times higher than on the much smaller bead, conventional fast-flow agarose (Sepharose) ion exchangers are achieved. Even at high loading velocities, the binding capacity changes only slightly (FIG. 1A). The media also exhibit high capture efficiency for feeds containing very low levels of the target protein. This eliminates the need for a concentration step.

Another important issue to be addressed is the inhibitory effect of cellular materials on the protein binding capacity of the capture large bead media. This effect is independent from the derivatization type of the beads and reduces protein binding capacities as a function of the cell concentration in the feed stream. We have developed a processing aid which when mixed into the feed stream at a concentration range of 0.01 to 1%, most preferably 0.05% to 0.4%, allows the utilization of the full capacity of the capture resin to bind the product from the feed stream.

The processing aid is a polymer, most preferably a low molecular weight agarose polymer, which blocks binding sites on the cell surfaces thereby preventing them from binding to the beads and blocking the bead surface for product capture. Derivatized agarose or other suitable polymers could also be used in preventing cellular materials from interacting with the bead surfaces.

When the 100–300 µm size range beads are derivatized with ion exchange groups, the dynamic protein binding capacity is further increased (FIG. 1B). The Q media offer protein binding capacities up to four times higher than conventional fast-flow agarose (Sepharose) ion exchange gels. At high loading velocities (500 cm/h), the binding capacity is still 3 times higher than fast-flow agarose (FIG. 1B).

Figure 2:
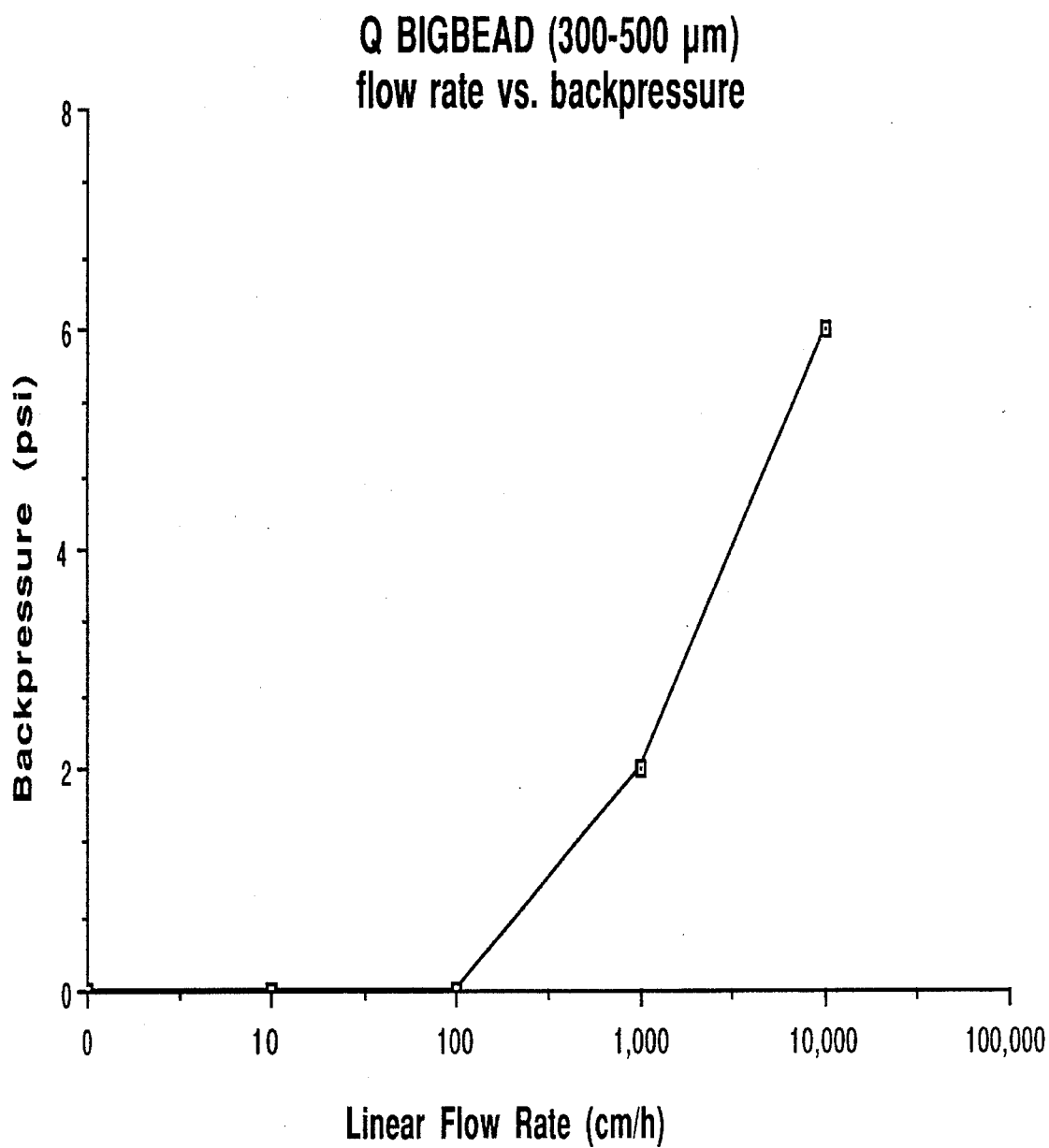
FIG. 2 shows a flow rate test in which a 9 ml bed volume Q BIG BEAD™ column (1.5 cm diameter) was used. Running buffer was 0.9% saline. Back pressure on the column was measured at selected linear velocities.

DEAE anion exchange cellulose is widely used in bioprocessing because of its high capacity. Large bead DEAE agarose has higher static capacity than the highest capacity cellulose anion exchanger (FIG. 2). It also maintains excellent dynamic capacities at high linear velocities at which cellulose ion exchangers lose all their binding capacity. This makes anion exchange BIGBEAD™ agarose media an optimal process chromatography tool for high-volume feed applications. Because of its high capacity, both very dilute and highly concentrated process liquors can be readily processed.

The large bead ion exchangers are stable with all commonly used buffers and reagents including high salt, 1M NaOH, high concentrations of denaturants (urea or guanidine) or organic solvents. The beads are stable between pH 2–14. They are regenerated in situ with 1M NaCl without repacking the column bed. After regeneration, the column is re-equilibrated with starting buffer. The column can be cleaned periodically with 0.5–1M NaOH to remove accumulated lipids, entrapped cellular debris and precipitated proteins. This treatment also reduces bacterial contaminants.

The large bead ion exchange media offer many advantages for bioprocessing. They allow simultaneous cell removal and capture of expressed proteins from cell culture or fermentation harvests as well as other unclarified feeds, thus cutting out centrifugation and/or filtration. Product losses typical to centrifugation and filtration are averted; with shorter processing cycles, productivity can also be significantly improved.

The large bead ion exchange media can be used in packed bed, standard low pressure chromatography columns, which simplifies operation and maintenance. In addition, the higher capacity of the ion exchange BIGBEADS allows the use of smaller columns with the same throughput. This reduces both the size of chromatography hardware needed, as well as the volume of buffers used in every cycle of operation.

The high capture efficiency of the BIGBEADs eliminates the need for a volume-reducing ultrafiltration step. The unique binding characteristics of the ion exchange BIGBEADs allow sample loading at high linear velocities, important in high-volume feed processing.

The isolation of the product from the crude feed stream can also be achieved on open columns. An example of the open column is a tank having a porous mesh at the bottom. The beads are placed in the tank and the feed is either run through it or stirred in the tank with the beads. Adsorption of the product takes place after which the tank is drained and the beads are washed and eluted.

The adsorptive matrix may also be a membrane or mesh having sufficiently large pores through which the particulate matter can exit. Washing and elution is then carried out as discussed earlier. It is obvious that derivatization methods are other than ion exchange can be used in functionalizing the beads.

Other example of derivatization may involve affinity or hydrophobic modifications of the beads, to produce a large bead chromatography medium functionalized with affinity or hydrophobic groups. Many examples of modification of chromatography matrices for affinity chromatography are well known in the art, and need not be described further in detail. To give a few examples, chromatographic matrices can be activated with cyanogen bromide or with groups that introduce N-hydroxysuccinimide esters. Other coupling reagents such as N,N'-carbonyl diimidazole can also be used. In some applications, it is desirable to introduce a spacer between the matrix and the ligand in order to prevent steric hindrance from interfering from the binding.

The adsorptive BIGBEAD™ matrix can also be used to process biological fluids in vivo. Affinity derivatized BIGBEAD can be a useful tool in this regard. An example for this is body fluids, such as blood or lymph. In a variety of diseased states or during invasive treatments, such as surgery, non-physiological substances may gain entry into the body. Specific removal of these substances from the circulation may reverse the diseased state or alleviate the symptoms of the disease.

In conclusion, the subject invention offers a novel, greatly simplified solution to the initial stages of separations in bioprocesses or other applications where particulate material is present in the feed stream. The lengthy and costly recovery operation is replaced with a single step process which combines particle removal, filtration, and concentration steps in a standard chromatography operation. The high dynamic capacities of adsorbents allow high volume feed processing and consequently high thoughput operations.

EXAMPLES

The following Examples are offered by way of illustration and not by way of limitation.

EXAMPLE 1

Purifying of monoclonal antibody from cell culture harvest by ion exchange

Figure 3:
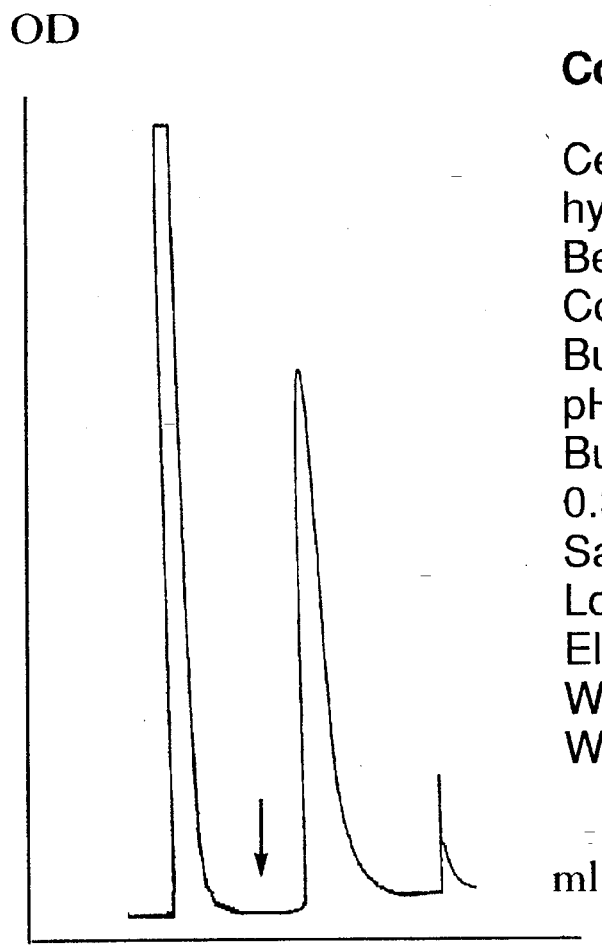
FIG. 3 is a chromatogram showing the separation of monoclonal antibody from hybridoma culture harvest. In the experiment, a protein-free hybridoma cell culture harvest was diluted 1:2 with deionized water and pH-adjusted to 5.0 with acetic acid. The IgG monoclonal antibody concentration in the feed was 10 μg/ml. The sample was chromatographed on a SP BIGBEAD™ (300–500 μm) column. After washing, the antibody was eluted with a 93% yield.

A protein-free hybridoma cell culture harvest was diluted 1:2 with deionized water and pH-adjusted to 5.0 with acetic acid. The IgG monoclonal antibody concentration in the feed was 10 µg/ml. The sample was chromatographed on a SP BIGBEAD™ column (300–500 µm). After washing, the antibody was eluted (FIG. 3) with 93% yield.

EXAMPLE 2

Purifying of albumin from a yeast suspension

Figure 4:
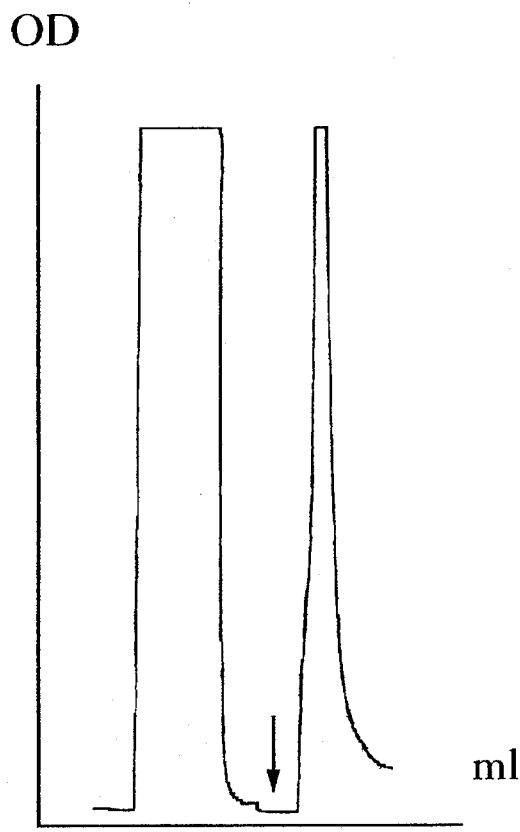
FIG. 4 is a chromatogram illustrating the separation of serum albumin from yeast cell suspension. A yeast cell slurry at $10^8$ cells per ml containing 1 mg/ml bovine serum albumin was applied to a Q BIGBEAD™ column and chromatographed. After washing, albumin was eluted at a yield of 96%.

A yeast cell suspension containing 1 mg/ml bovine serum albumin was applied to a Q CELLTHRU BIGBEAD™ (300–500 µm) column and chromatographed. After washing, albumin was eluted (FIG. 4) at a yield of 96%.

EXAMPLE 3

Purifying of recombinant Fab from fermentation broth

Figure 5:
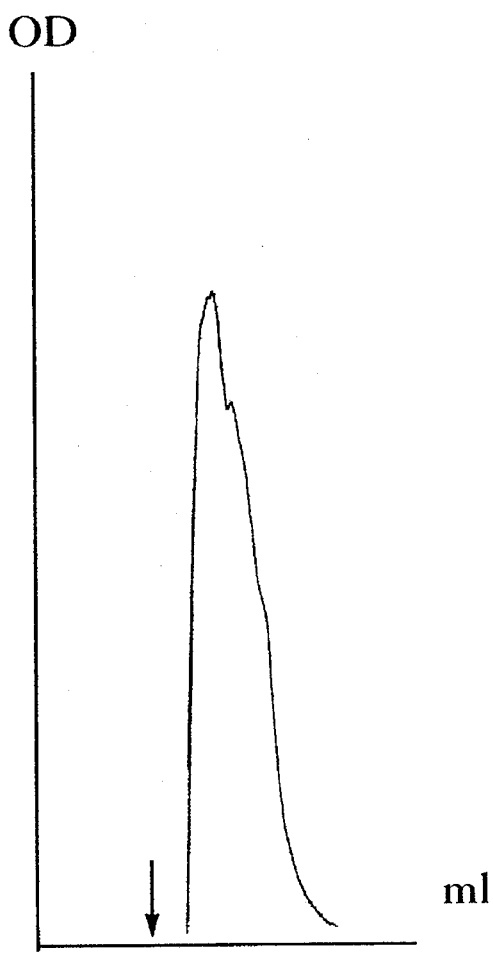
FIG. 5 is a chromatogram of the separation of recombinant Fab from fermentation broth. Recombinant *E. coli* fermentation broth (OD=100) containing a Fab-toxin conjugate was diluted 1:2 with 20 mM citrate at pH 5.0, and chromatographed on a SP9 BIGBEAD™ column. After washing, the product was eluted.

Recombinant *E. coli* fermentation broth (OD=100) containing a Fab-toxin conjugate was diluted 1:2 with 20 mM citrate at pH 5.0, and chromatographed on a SP BIGBEAD™ column (800–1100 µm). After washing, the product was eluted (FIG. 5).

EXAMPLE 4

Ion removal from protein-free tissue culture medium/harvest

Into 100 ml of protein-free culture medium the ion removing BIGBEAD™ resin was mixed at increasing concentrations and gently agitated for 20 min. Conductivity and pH were measured throughout the procedure. The conductivity was gradually reduced with increasing concentrations of the beads. At the ratio of 0.15 ml resin per ml culture medium, the conductivity was reduced to 4–5 mS (FIG. 6) at which SP BIGBEAD can completely adsorb monoclonal antibody from the medium.

EXAMPLE 5

Ion removal from blood plasma

Into 100 ml of plasma the ion removing BIGBEAD™ resin was mixed at increasing amounts and gently agitated for 20 min. Conductivity and pH were measured. The conductivity was gradually reduced with increasing concentrations of the beads. At the ratio of 0.2 ml resin per ml serum, the conductivity was reduced to 3–4 mS (FIG. 7) at which DEAE BIGBEAD™ (100–300 µm) can effectively adsorb albumin from the serum.

EXAMPLE 6

Purifying of serum albumin on DEAE BIGBEAD (100–300 µm)

Figure 6:
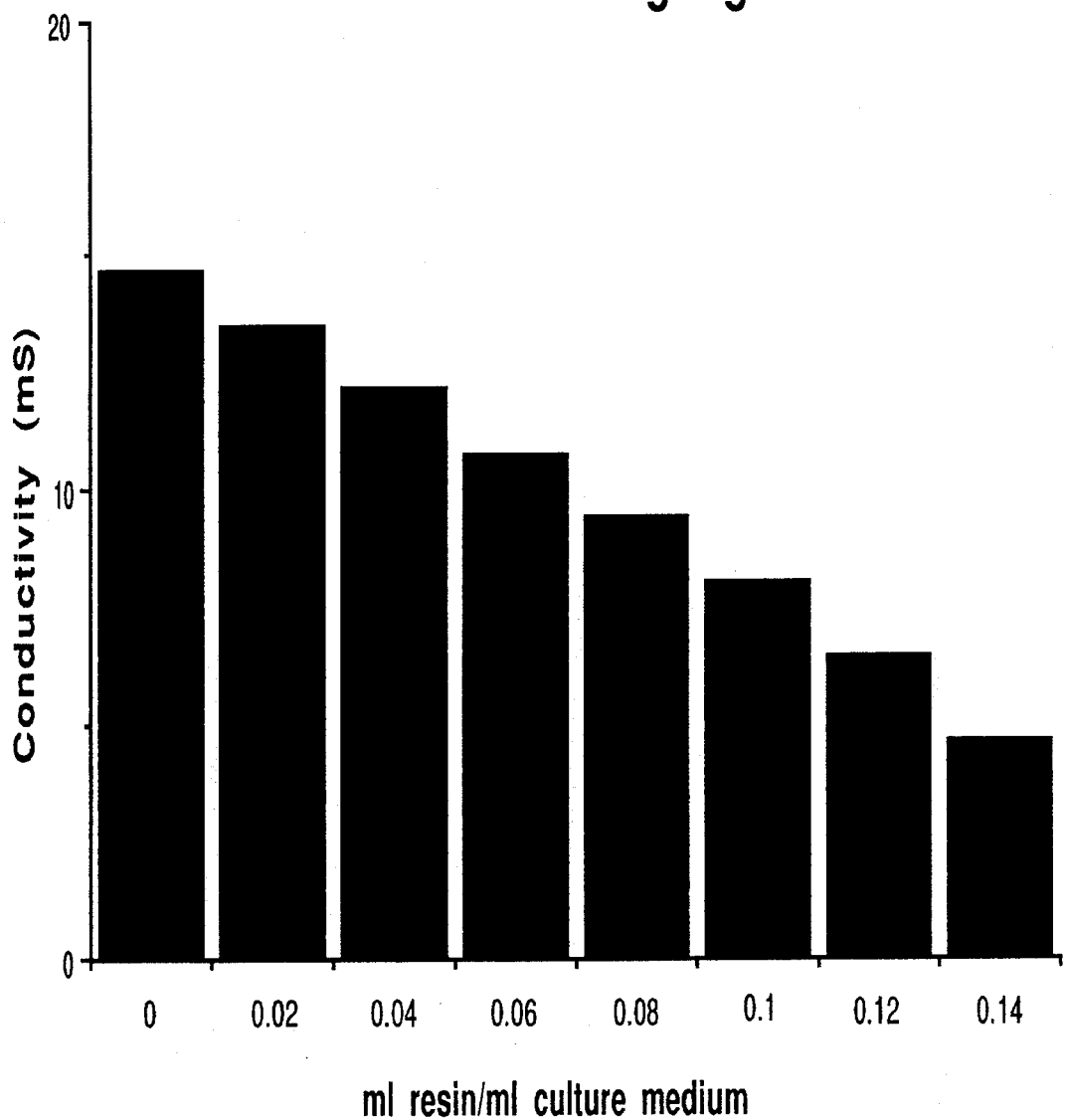
FIG. 6 is a graph demonstrating how the conductivity of protein-free hybridoma cell culture medium was reduced with the addition of increasing volumes of ion removing BIGBEAD™ resin. Approximately 0.15 ml resin added per ml medium needed to lower conductivity to the 4–5 mS range required for direct capture of monoclonal antibody from hybridoma cell culture harvest on SP BIGBEAD™.

Swine serum, 20 ml, was treated batchwise with 4 ml ion removing BIGBEADs for 20 min. During treatment, the sample conductivity was reduced from 19.8 mS to 2.7 mS. The beads were separated on a large pore filter and the treated serum chromatographed on a DEAE BIGBEAD™ column, equilibrated with 20 mM phosphate, pH 7.0 buffer. After washing with equilibration buffer, bound albumin was eluted with a 20 mM phosphate, 0.3M NaCl, pH 7.0 buffer. In the column flowthrough, an IgG rich fraction was obtained and in the eluate an albumin rich fraction was obtained (FIG. 6). The purity of albumin was 85–90% by SDS-PAGE (not shown) with a yield of approximately 95%.

EXAMPLE 7

Purification of monoclonal antibody on Protein A BIGBEAD (300–500 µm)

Hybridoma cell culture harvest was applied to a Protein A BIGBEAD™ column at 60 cm/h. The IgG monoclonal antibody concentration in the feed was 10 µg/ml. The sample was chromatographed and after washing the antibody was eluted with a 91% yield.

EXAMPLE 8

Removal of heparin from whole blood

Sixty ml of freshly drawn blood was spiked with heparin at 5 U/ml and passed through a 2 ml bed volume protamine derivatized BIGBEAD™ (300–500 µm as well as 500–800 µm sizes) column at 4 ml/min. Heparin level was measured in the column effluent by the colorimetric Kabi test and found to be 0.8 U/ml. The result demonstrates that extraneous materials can be removed from whole blood on the large bead chromatography media.

ADVANTAGES OF THE INVENTION

The invention represents a significant improvement in the processing of unclarified biological materials. It allows direct processing of crude feeds, such as cell culture/fermentation harvests tissue extracts, or blood plasma, on packed bed columns, and accomplishes ion removal from crude samples without dilution and the resulting loss of throughput. The invention provides rapid and efficient methods for performing the initial steps of purification or extraction of molecules of biological interest, particularly proteins such as enzymes, antibodies, and receptor proteins. It will be understood that in giving the preferred embodiment and application of the invention, the concept and scope of the invention is not limited to the specific reagents but certain changes and modifications may be practical within the scope of the appended claims.

We claim:

1. A method for the direct capture of soluble product from an unclarified process liquor using large bead chromatography media in packed bed columns comprising the steps of:

(a) packing a large bead capture chromatography medium into low pressure chromatography columns;

(b) conditioning an unclarified process liquor having a high physiological ionic strength and containing a desired soluble product so that the product can be adsorbed onto the capture chromatography medium;

(c) applying the conditioned process liquor mixed with the processing aid onto the chromatography column under conditions such that the soluble product adsorbs to the capture chromatography medium;

(d) allowing particulate materials in the unclarified process liquor to exit the column in the interparticle space;

(e) removing residual entrapped particles from the column via high speed reverse wash pulses; and (vi) eluting product from the capture chromatography medium by changing binding conditions so that the product is removed from the column.

2. The method of claim 1 wherein the unclarified process liquor contains at least one component selected from the group consisting of cells, cell fragments, aggregated proteins, denatured proteins, precipitated proteins, lipids, and nucleic acids.

3. The method of claim 2 wherein the cells are of bacterial, yeast, or mammalian origin.

4. The method of claim 3 wherein the cells are mammalian cells and are blood cells.

5. The method of claim 3 wherein the conditioning step is performed using a large bead mixed bed ion exchanger capable of capturing both small cations and anions and replacing them with water.

6. The method of claim 5 wherein the large bead mixed bed ion exchange resin has capacity for the product sufficiently low so that less than about 5% of the protein loaded is bound.

7. The method of claim 5 wherein said large bead mixed bed ion exchange resin is made out of polymers, silica or natural compounds.

8. The method of claim 1 wherein said conditioning step reduces the high physiological ionic strength of the process liquor to a level sufficient to achieve binding of the product to the large bead chromatography medium.

9. The method of claim 1 wherein the bead size range of the capture chromatography medium is from about 100 μm to about 1100 μm.

10. The method of claim 9 wherein the bead size range of the capture chromatography media is from about 100 μm to about 300 μm.

11. The method of claim 9 wherein the bead size range of the capture chromatography media is from about 300 μm to about 500 μm.

12. The method of claim 9 wherein the bead size range of the capture chromatography media is from about 500 μm to about 800 μm.

13. The method of claim 12 wherein the loss of binding capacity of the capture medium is less than 30% from static to 500 cm/h linear velocity.

14. The method of claim 9 wherein the bead size range of the capture chromatography media is from about 800 μm to about 1100 μm.

15. The method of claim 9 wherein the large bead capture medium maintains high dynamic product binding capacities in the linear velocity range of 1–1000 cm/h.

16. The method of claim 1 wherein the desired product is a protein.

17. The method of claim 1 wherein said large bead chromatography resin is made out of polymers, silica or natural compounds.

18. The method of claim 1 wherein said large bead capture chromatography medium is functionalized with a group selected from affinity, hydrophobic, and ion exchange groups.

19. The method of claim 1 wherein said processing aid has the capacity to overcome the inhibitory effect of cellular material on product binding during capture.

20. The method of claim 19 wherein said processing aid is a polysaccharide or a derivative thereof.

21. The method of claim 19 wherein said processing aid is agarose or a derivative thereof.

* * * * *